(12) United States Patent
Breithardt et al.

(10) Patent No.: US 7,181,270 B2
(45) Date of Patent: Feb. 20, 2007

(54) ARRANGEMENT FOR PREDICTING TACHYARRHYTHMIA

(75) Inventors: Guenter Breithardt, Muenster (DE); Thomas Fetsch, Stockdorf (DE); Joerg Fregien, Hoenow (DE); Thomas Doerr, Berlin (DE); Tino Hauser, Berlin (DE)

(73) Assignee: Biotronik Mess- und Therapiegeraete GmbH & Co. Ingeniuerbuero Berlin, Berlin (DE)

( * ) Notice: Subject to any disclaimer, the term of this patent is extended or adjusted under 35 U.S.C. 154(b) by 625 days.

(21) Appl. No.: 10/268,038

(22) Filed: Oct. 9, 2002

(65) Prior Publication Data

US 2003/0074028 A1   Apr. 17, 2003

(30) Foreign Application Priority Data

Oct. 13, 2001   (DE)   ................................ 101 51 089

(51) Int. Cl.
*A61N 1/362* (2006.01)
(52) U.S. Cl. ...................................... 600/518; 600/515
(58) Field of Classification Search ................ 600/518, 600/515; 607/9, 14
See application file for complete search history.

(56) References Cited

U.S. PATENT DOCUMENTS

| | | | |
|---|---|---|---|
| 4,880,005 A | | 11/1989 | Pless |
| 5,086,772 A | * | 2/1992 | Larnard et al. ................. 607/4 |
| 5,560,370 A | * | 10/1996 | Verrier et al. ................ 600/518 |
| 5,749,900 A | * | 5/1998 | Schroeppel et al. ........... 607/4 |
| 5,967,995 A | | 10/1999 | Shusterman |
| 6,115,627 A | | 9/2000 | Street |
| 6,181,966 B1 | * | 1/2001 | Nigam .......................... 607/4 |
| 6,519,490 B1 | * | 2/2003 | Wiesel ....................... 600/518 |
| 2005/0187586 A1 | * | 8/2005 | David et al. ................... 607/9 |
| 2005/0234518 A1 | * | 10/2005 | Heruth et al. .................. 607/6 |

OTHER PUBLICATIONS

De Bruyne, et al., "Both decreased and increased heart rate variability on th standard 10-second electrocardiogram predict cardiac mortality in the elderly," Amer. J of Epidemiology, The Johns Hopkins University (USA), vol. 150 ( No. 12), p. 1282-1288, (Dec. 15, 1999).

Aysin, et al, "Detection of Transients in Heart Rate Variability Signals Using a Time-Varying Karhunen-Loeve Expansion," IEEE (USA), p. 3586-3589, ( Oct. 2, 2000).

(Continued)

*Primary Examiner*—Robert Pezzuto
*Assistant Examiner*—Shevon Johnson
(74) *Attorney, Agent, or Firm*—Hahn Loeser & Parks, LLP

(57) ABSTRACT

An arrangement 10 for predicting tachyarrhythmia of a heart has a detection means 12 and an evaluation unit 18. The detection means 12 picks up electrical signals from the heart. The evaluation unit 18, which is connected to the detection means, determines a rate value that depends upon the respective heart rate. The evaluation unit also evaluate a plurality of correspondingly determined rates values, to determine a heart rate variability value that depends on the variability of the detected rate values, wherein the evaluation unit 18 responds to a rise in the heart rate variability value.

20 Claims, 1 Drawing Sheet

OTHER PUBLICATIONS

Hoeher, et al, "Heart-Rate Dependency of QRS Microvariability during Atrial Pacing," Computers in Cardiology, IEEE (USA), No. 27, p. 727-730, (Oct. 2, 2000).

Pruvot, et al., "Heart Rate Dynamics at the Onset of Ventricular Tachyarrhymias as Retrieved from Implantable Cardioverter-Defibrillators in Patients with Coronary Artery Disease," Circulation, AHA (USA), p. 2398-2404, (May 23, 2000).

Huikuri, "Heart Rate Dynamics and Vulnerability to Ventricular Tachyarrhymias," Annals of Medicine, The Finnish Medical Society, p. 321-325, (Oct. 2, 1997).

Fei, et al., "Change of Autonomic Influence on the Heart Immediately before the Onset of Spontaneous Idiopathic Ventricular Tachycardia," JACC, American College of Cardiology (USA), vol. 24 (No. 6), p. 1515-1522, (Oct. 2, 1994).

* cited by examiner

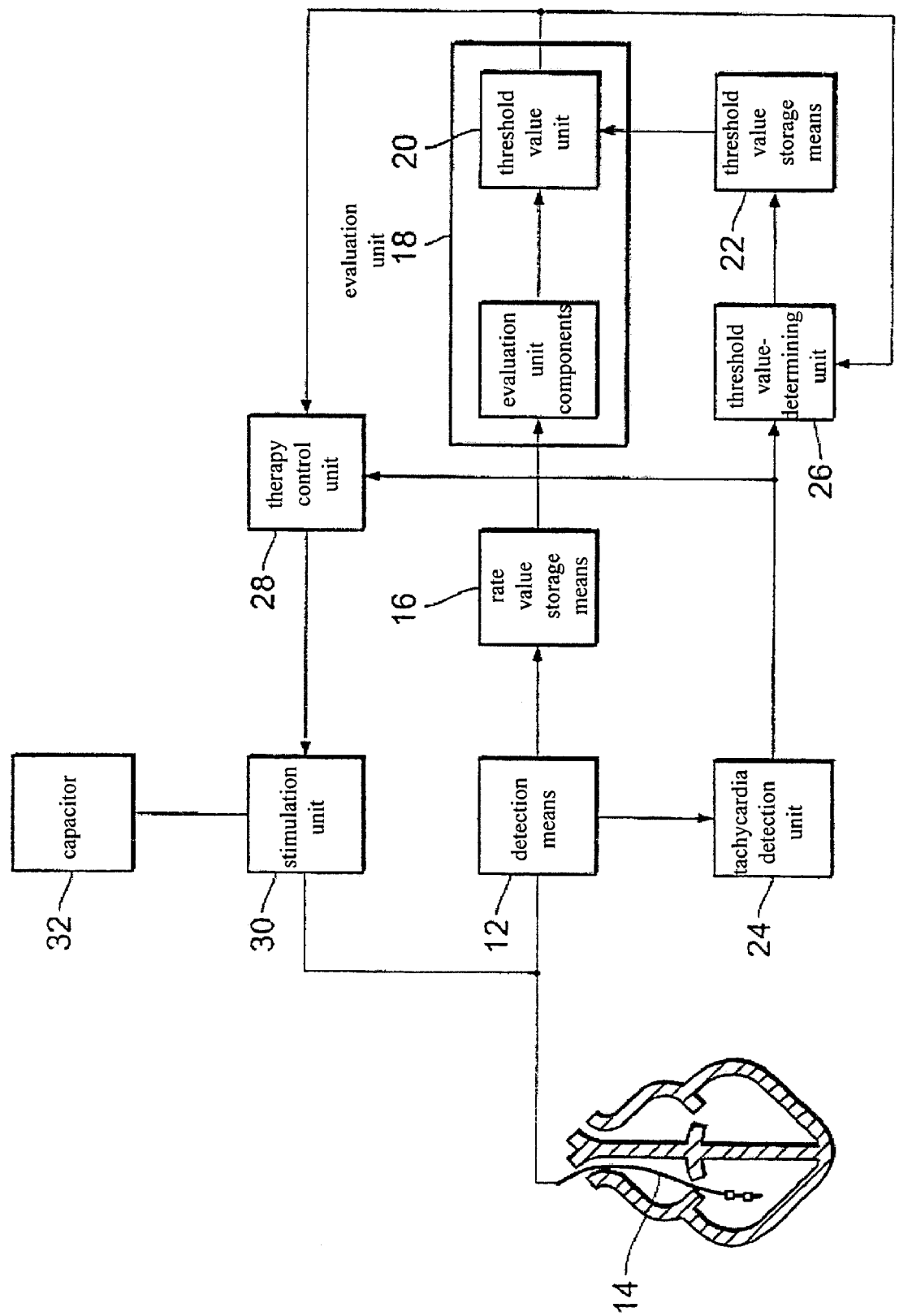

ARRANGEMENT FOR PREDICTING TACHYARRHYTHMIA

The invention concerns an arrangement for predicting tachyarrhythmia, which includes detection means adapted to pick up electrical signals from a heart and an evaluation unit connected to the detection means. The invention further concerns an electrical therapy device having an arrangement of that kind. In that respect the electrical therapy device is in particular a stimulator such as cardiac pacemaker, a cardioverter or a defibrillator.

BACKGROUND OF THE ART

Corresponding implantable therapy devices are basically known. They are usually adapted to detect electrical signals from the heart and to deliver electrical pulses to a heart. A corresponding detection unit for the electrical signals can be connected for that purpose to an electrode line which leads into a ventricle and/or an atrium of the heart.

Such an electrode line can be designed in known manner for uni-, bi- or multi-polar recording of electrical signals from the heart and for corresponding delivery of therapeutic current pulses to the heart. For example bipolar electrode lines are suitable for recording electrical signals from the heart, which electrode lines can be connected together with the detection unit in such a way that the detected signals are recorded in unipolar or bipolar mode. For the delivery of stimulation or defibrillation pulses to a heart, a therapy device of that kind usually includes a stimulation unit. The detection unit and the stimulation unit of such an implant are usually connected together by way of a control which controls the delivery of pulses to the heart in dependence on the electrical parameters picked up from the heart and possibly further parameters. Such further parameters, in the case of a rate-adaptive cardiac pacemaker, can be characteristic of the physiological demand of a patient.

For treating tachyarrhythmias, it is particularly known to implement an analysis of the heart rate variability. In accordance with U.S. Pat. No 5,749,900 a corresponding arrangement responds to a drop in the variability of the heart rate. Other arrangements for in part complicated and expensive analysis of a plurality of parameters are known for example from U.S. Pat. Nos. 5,967,995 and 6,115,627.

Suitable prediction of tachyarrhythmias is of interest in particular for implantable therapy devices in order for example to be able to trigger in good time preventive or prophylactic therapies.

The object of the present invention is to provide an arrangement for predicting tachyarrhythmia, which as far as possible complies with the above-indicated demands.

SUMMARY OF THE INVENTION

In accordance with the invention that object is attained by an arrangement of the kind set forth in the opening part of this specification, in which the evaluation unit is adapted to determine a rate value which is dependent on the respective heart rate and to evaluate a plurality of correspondingly determined rates values, in such a way that evaluation gives a heart rate variability value which depends on the variability of the detected rate values, wherein the evaluation unit responds to a rise in the heart rate variability value.

The invention is based on the surprising novel realization that more effective prediction of tachyarrhythmias is possible if, as a departure from the state of the art, a corresponding evaluation unit responds not to a fall in the heart rate variability but to a rise.

Alternatively or additionally the evaluation unit of the arrangement set forth in the opening part of this specification is adapted to detect a drop in the heart rate. Particularly reliable detection of a threatening tachyarrhythmia which already occurs up to half an hour before the occurrence thereof can be achieved by a combination of detection of a rise in heart rate variability with simultaneous detection of the fall in the heart rate or frequency. Both detection criteria—rise in the heart rate variability and drop in the heart rate—can however each be implemented in itself by virtue of a suitable design configuration of the evaluation unit.

Preferably the evaluation unit is adapted to detect a rise in the heart rate variability by 20%, particularly preferably by 30%. Additionally or alternatively it is adapted to detect a fall in the heart rate by 2%, preferably 5%.

In a preferred alternative configuration the evaluation unit is adapted to form a standard deviation in the rate values as a heart rate variability value. The arrangement correspondingly responds to a rise in that standard deviation.

In order to be able to effectively form the heart rate variability value and/or effectively determine a change in the heart rate, a preferred embodiment of the arrangement includes a rate value storage means which is adapted to store a plurality of successive rate values and which is at least indirectly connected to the detection means and the evaluation unit, wherein the detection means, the evaluation unit and the rate value storage means co-operate in such a way that a respectively current sequence of rate values is stored in the rate value storage means and the evaluation unit calculates the heart rate variability value and/or the relative change in the heart rate on the basis of the rate values in the rate value storage means. It is particularly preferred if in that case the evaluation unit is adapted to determine the heart rate variability value with each new freshly detected rate value.

A preferred embodiment further includes a threshold value unit which is connected to or integrated into the evaluation unit and which is adapted to compare each heart rate variability value to a predetermined threshold value and to produce a tachycardia warning signal when the threshold value is exceeded. This embodiment preferably has a threshold value storage means which is adapted to store the threshold value and is connected to the threshold value unit. The threshold value storage means can be designed to be re-writable so that the threshold value can be adapted to the respectively currently prevailing situation by a physician.

The arrangement further preferably includes a tachycardia detection unit which is connected to the detection unit and which is adapted to detect an acute tachycardia and to output a tachycardia signal.

An arrangement which has both a threshold value storage means and also the above-mentioned tachycardia detection unit preferably further has a threshold value determining unit which is connected to the threshold value storage means and the tachycardia detection unit and which is adapted to alter the threshold value in the threshold value storage means if the tachycardia detection unit outputs a tachycardia signal without the threshold value unit having previously outputted a tachycardia warning signal associated with acute tachycardia. Such a configuration of the arrangement advantageously permits the automatic formation of a suitable threshold value in such a fashion that if possible a tachycardia warning signal is also outputted prior to an acute tachycardia.

In addition, there is preferably provided a therapy control unit which is connected to the threshold value unit or the evaluation unit respectively and includes a stimulation unit, wherein the therapy control unit is so designed that it triggers prophylactic stimulation in the ventricle at a frequency which is above the base frequency if a tachycardia warning signal is present. If the arrangement also includes a tachycardia detection unit, the therapy control unit is preferably connected thereto and is so designed that it triggers an anti-tachycardiac therapy or a defibrillation procedure if acute tachycardia is indicated by a tachycardia signal from the tachycardia detection unit.

An arrangement of the above-indicated kind is preferably a component part of an electrical therapy device, in particular a stimulator such as for example a cardiac pacemaker, a cardioverter or a defibrillator.

BRIEF DESCRIPTION OF THE DRAWINGS

The invention will now be described in greater detail by means of an embodiment with reference to the single FIGURE.

The FIGURE shows an implantable cardioverter/defibrillator (ICD).

DETAILED DESCRIPTION OF A PREFERRED EMBODIMENT

The electrical therapy device shown in FIG. 1 in the form of an implantable cardioverter/defibrillator (ICD) 10 includes detection means 12 for detecting electrical signals from a heart by way of an electrode line 14 which for example extends into the right ventricle of a heart. The detection means 12 are accordingly connected or at least are connectable at the input side to the electrode line 14. The detection means 12 include the usual means for recording an intracardial electrocardiogram such as for example an input amplifier, and a QRS detector in order to detect the QRS complex in the intracardially recorded electrocardiogram. The arrangement further includes time-determining means which co-operate with the QRS detector in such a way that the detection means 12 can determine the respectively current heart rate from the spacing of a R-blip of the QRS complex relative to the R-blip of the next following QRS complex. The current heart rate value which is respectively determined in that way is outputted into a rate value storage means 16 which is connected to the output of the detection means 12 and which is adapted to store a predetermined number of the most current heart rate values.

Connected on the output side of the rate value storage means 16 is an evaluation unit 18, which includes or is connected to a threshold value unit 20. The evaluation unit 18 is adapted to form, from the respectively current heart rate values stored in the rate value storage means 16, a standard deviation in respect of those rate values. A value corresponding to that standard deviation is fed to the threshold value unit 20.

In the preferred embodiment the evaluation unit is additionally adapted to ascertain a respectively current, relative change in the heart rate from the respectively current heart rate values stored in the rate value storage means 16. A value corresponding to that relative heart rate change—for example a reduction in the heart rate by 5%—is also passed to the threshold value unit 20. For the purposes of ascertaining the relative heart rate change for example a current value in respect of the heart rate is compared to and related to a rate value which is averaged over a predetermined period of time. The averaged rate value is also adapted with each new rate detection.

In specific terms for example the 5 or 10 respectively most current heart rate values are stored in the rate value storage means 16. On the basis of those values, on the one hand the variability of the heart rate is ascertained, insofar as the standard deviation is formed for those values. Secondly, the most current of the rate values is related to the mean value of all 5 or 10 stored rate values in order to determine the respectively current, relative rate change.

The threshold value unit 20 is connected to a threshold value storage means 22 and is adapted to compare the respectively current value of the standard deviation and the relative heart rate change to a respective value stored in the threshold value storage means 22, and to output a tachycardia warning signal if the current standard deviation in respect of the heart rate values exceeds the reference value stored in the threshold value storage means 22 and at the same time or in close time proximity a relative drop in the heart frequency exceeds a threshold value which is also stored, corresponding for example to a 3% frequency drop.

Just the detection of a rise in heart rate variability above a threshold value represents a crucial difference in relation to the prevailing teaching, as the prevailing teaching is based on a drop in heart rate variability. Advantageously, a relative drop in heart frequency is detected at the same time. The latter however is not absolutely necessary.

The tachycardia warning signal is fed to a therapy control unit 28 which, when the tachycardia warning signal is applied, causes prophylactic stimulation to be triggered in the ventricle at a frequency which is above the base frequency. That is implemented by a stimulation unit 30 having a capacitor 32 as an energy storage means, which is adapted to deliver electrical pulses to the ventricle of a heart for therapy of the threatening tachycardia, by way of the electrode line 14. In a corresponding manner the stimulation unit 30 is also connected to the electrode line 14.

In order to be able to automatically form a suitable threshold value for the threshold value unit 20 and store it in the threshold value storage means 22, the threshold value storage means 22 is connected at the input side to a threshold value-determining unit 26 which in turn is adapted to receive two input signals, more specifically a tachycardia signal which is formed by a tachycardia detection unit 24 in the case of an acute tachycardia, and the tachycardia warning signal which is generated by the evaluation unit or the threshold value unit 20 thereof. For that purpose the tachycardia detection unit is connected at the input side to the detection means 12. As a second input signal the threshold value-determining unit 26 receives the tachycardia warning signal from the threshold value unit 20. If a tachycardia signal which indicates acute tachycardia, from the tachycardia detection unit 24, is applied to the threshold value-determining unit 26, without a tachycardia warning signal from the threshold value unit 20 having been previously outputted, the threshold value-determining unit causes a drop in the threshold value in the threshold value storage means 22. The aim of this is that the threshold value unit already responds to smaller rises in the standard deviation of the heart rate values so that it already earlier outputs a tachycardia warning signal.

What is claimed is:

1. An arrangement for predicting tachyarrhythmia of a heart, comprising:
   means for detecting, to pick up electrical signals from the heart;
   an evaluation unit connected to the detection means,
      wherein the evaluation unit determines a rate value that depends on a heart rate of the heart and evaluates a plurality of correspondingly determined rates values, such that the evaluation process determines a drop in heart rate, and/or a heart rate variability value that depends on the variability of the detected rate values such that a relative rise in the heart rate variability value may be responded to; and a threshold value unit, connected to or integrated into the evaluation unit, which
compares each relative heart rate variability value and/or the drop in heart rate to a respectively predetermined threshold value and produces a tachycardia warning signal when the relative heart rate variability value increases above the corresponding relative threshold value, and/or when the threshold value corresponding to the drop in heart rate is exceeded, said tachycardia warning signal thus being a predictive indicator of a future tachyarrhythmia of the heart.

2. The arrangement of claim 1, wherein:
the evaluation unit calculates a standard deviation of the rate values to serve as the heart rate variability value.

3. The arrangement of claim 2, further comprising:
a means for storing, to store a plurality of successive rate values, said rate value storage means being at least indirectly connected to the detection means and the evaluation unit;
wherein the detection means, the evaluation unit and the rate value storage means co-operate in such a way that a respectively current sequence of rate values is stored in the rate value storage means and the evaluation unit calculates the heart rate variability value and/or the drop in the heart rate based on the rate values stored in the rate value storage means.

4. The arrangement of claim 3, wherein:
the evaluation unit determines the heart rate variability value and/or the drop in the heart rate with each freshly detected rate value.

5. The arrangement of claim 1, wherein:
the threshold value unit detects a rise in the relative heart rate variability value of more than 20%.

6. The arrangement of claim 5, further comprising:
a therapy control unit, connected to the threshold value unit; and
a stimulation unit having an energy storage means;
wherein the therapy control unit triggers a prophylactic stimulation when a tachycardia warning signal occurs.

7. The arrangement of claim 5, further comprising:
a threshold value storage means, to store the threshold value or values, connected to the threshold value unit.

8. The arrangement of claim 7, further comprising:
a tachycardia detection unit, connected to the detection unit, to detect an acute tachycardia and to output a tachycardia signal.

9. The arrangement of claim 8, further comprising:
a threshold value-determining unit, connected to the threshold value storage means and the tachycardia detection unit, to change the threshold value or values in the threshold value storage means if the tachycardia detection unit outputs a tachycardia signal without the threshold value unit previously having outputted a tachycardia warning signal associated with the acute tachycardia.

10. The arrangement of claim 8, further comprising:
a therapy control unit, connected to the threshold value unit; and
a stimulation unit having an energy storage means;
wherein the therapy control unit triggers a prophylactic stimulation when a tachycardia warning signal occurs.

11. The arrangement of claim 10, wherein:
the therapy control unit is connected to the tachycardia detection unit and triggers an anti-tachycardiac therapy or defibrillation if a tachycardia signal occurs.

12. The arrangement of claim 1, further comprising:
a threshold value storage means, to store the threshold value or values, connected to the threshold value unit.

13. The arrangement of claim 12, further comprising:
a tachycardia detection unit, connected to the detection unit, to detect an acute tachycardia and to output a tachycardia signal.

14. The arrangement of claim 13, further comprising:
a threshold value-determining unit, connected to the threshold value storage means and the tachycardia detection unit, to change the threshold value or values in the threshold value storage means if the tachycardia detection unit outputs a tachycardia signal without the threshold value unit previously having outputted a tachycardia warning signal associated with the acute tachycardia.

15. The arrangement of claim 1, further comprising:
a means for storing, to store a plurality of successive rate values, said rate value storage means being at least indirectly connected to the detection means and the evaluation unit;
wherein the detection means, the evaluation unit and the rate value storage means co-operate in such a way that a respectively current sequence of rate values is stored in the rate value storage means and the evaluation unit calculates the heart rate variability value and/or the drop in the heart rate based on the rate values stored in the rate value storage means.

16. The arrangement of claim 15, wherein:
the evaluation unit determines the heart rate variability value and/or the drop in the heart rate with each freshly detected rate value.

17. The arrangement of claim 1, wherein:
the threshold value unit detects a rise in the relative heart rate variability value of more than 30%.

18. The arrangement of claim 1, wherein:
the threshold value unit detects a drop in the heart rate by more than 2%.

19. The arrangement of claim 1, wherein:
the threshold value unit detects a drop in the heart rate by more than 5%.

20. An arrangement for predicting tachyarrhythmia of a heart, comprising:
means for detecting, to pick up electrical signals from the heart; an evaluation unit connected to the detection means,
wherein the evaluation unit determines a rate value that depends on a heart rate of the heart and evaluates a plurality of correspondingly determined rates values, such that the evaluation process determines a drop in heart rate, and/or a heart rate variability value that depends on the variability of the detected rate values such that at least a rise in the heart rate variability value may be responded to;

a threshold value unit, connected to or integrated into the evaluation unit, which compares each heart rate variability value and/or the drop in heart rate to a respectively predetermined threshold value and produces a tachycardia warning signal when the heart rate variability value increases above the corresponding threshold value, and/or when the threshold value corresponding to the drop in heart rate is exceeded, said tachycardia warning signal thus being a predictive indicator of a future tachyarrhythmia of the heart;

a threshold value storage means, to store the threshold value or values, connected to the threshold value unit;

a tachycardia detection unit, connected to the detection unit, to detect an acute tachycardia and to output a tachycardia signal; and a threshold value-determining unit, connected to the threshold value storage means and the tachycardia detection unit, to change the threshold value or values in the threshold value storage means if the tachycardia detection unit outputs a tachycardia signal without the threshold value unit previously having outputted a tachycardia warning signal associated with the acute tachycardia.

* * * * *